United States Patent
Sheen et al.

(10) Patent No.: US 6,969,851 B1
(45) Date of Patent: Nov. 29, 2005

(54) ION-MOBILITY SPECTROMETRY SENSOR FOR NOX DETECTION

(75) Inventors: Shuh-Haw Sheen, Naperville, IL (US); Apostolos C. Raptis, Downers Grove, IL (US); Hual-Te Chien, Naperville, IL (US)

(73) Assignee: The University of Chicago, Chicago, IL (US)

( * ) Notice: Subject to any disclaimer, the term of this patent is extended or adjusted under 35 U.S.C. 154(b) by 33 days.

(21) Appl. No.: 10/920,539

(22) Filed: Aug. 18, 2004

(51) Int. Cl.[7] .......................... H01J 49/26; G01N 23/00
(52) U.S. Cl. ................. 250/288; 250/286; 313/231.41; 315/111.21; 422/83; 436/116
(58) Field of Search ............................... 250/288, 286; 313/231.41; 315/111.21; 422/83; 436/116

(56) References Cited

U.S. PATENT DOCUMENTS

2004/0126872 A1 * 7/2004 Miller et al. .................. 422/83

* cited by examiner

Primary Examiner—Nikita Wells
(74) Attorney, Agent, or Firm—Joan Pennington

(57) ABSTRACT

A sensor and detection methods are provided for detecting nitric oxides (NOx) in an exhaust gas based upon ion mobility spectrometry (IMS) technique. An ionization chamber having an interior electrically conductive shell receives exhaust gas. A spark electrode having a needle tip extends into the ionization chamber. A shutter grid is coupled between the ionization chamber and an ion drift tube. A substantially continuous spark discharge is established between the electrically conductive shell and the needle tip of the spark electrode for ionization of the exhaust gas. Negative $NO_2$ ions are kept inside the chamber by biasing the electrically conductive shell and the shutter grid at a negative voltage. Then a positive pulse is applied to the shutter grid to cause the shutter to open for negative $NO_2$ ions to exit into the ion drift tube. The IMS sensor is small-sized, low-cost, robust, and reliable.

20 Claims, 3 Drawing Sheets

ION-MOBILITY SPECTROMETRY SENSOR FOR NOX DETECTION

The United States Government has rights in this invention pursuant to Contract No. W-31-109-ENG-38 between the United States Government and Argonne National Laboratory.

FIELD OF THE INVENTION

The present invention relates to a sensor and detection methods for detecting nitric oxides (NOx), and more particularly to a Nox detection sensor based upon ion mobility spectrometry (IMS) technique.

DESCRIPTION OF THE RELATED ART

A typical IMS instrument consists of an ionization source, an ion drift tube and an ion detector. The instrument produces an ion spectrum from which ion drift time and peak amplitude are measured and related to ion characteristics. Commercial IMS instruments use a radioactive ionization source, typically $^{63}Ni$, and require a vacuum in the drift tube, making the instrument impractical and expensive. Thus the current IMS instrument cannot be used as an automobile exhaust emission sensor.

Today, the need of NOx emission sensor is pronounced and urgent. Low-cost semiconductor NOx sensors generally suffer from (1) difficulty to function in a harsh environment, including for example, high temperature, pressure, and humidity, (2) problems of long-term stability, and (3) slow response and recovery times.

A principal object of the present invention is to provide an improved sensor and detection methods for detecting nitric oxides (NOx).

Other objects of the present invention are to provide such improved sensor and detection methods for detecting nitric oxides (NOx) substantially without negative effect and that overcome some disadvantages of prior art arrangements.

SUMMARY OF THE INVENTION

In brief, a sensor and detection methods are provided for detecting nitric oxides (NOx) in an exhaust gas based upon ion mobility spectrometry (IMS) technique. The IMS sensor includes an ionization chamber receiving the exhaust gas. The ionization chamber includes an interior electrically conductive shell. A spark electrode having a needle tip extends into the ionization chamber. A shutter grid is coupled between the ionization chamber and an ion drift tube. A substantially continuous spark discharge is established between the electrically conductive shell of the ionization chamber and the needle tip of the spark electrode.

In accordance with features of the invention, during a negative mode of operation, negative $NO_2$ ions produced in the discharge region are kept inside the chamber by biasing the electrically conductive shell of the ionization chamber and the shutter grid at a negative voltage. Then a positive pulse is applied to the shutter grid to cause the shutter to open for negative ions to exit into the ion drift tube. The pulse frequency is selected so that equilibrium between ion production and extraction is established. To detect positive NO ions, a positive mode of operation is used. In the positive mode of operation, opposite polarity voltages are applied as compared to the negative mode of operation.

In accordance with features of the invention, the IMS sensor is small-sized, low-cost, robust, and reliable. A thermoelectric Peltier plate optionally is used to condition the exhaust gas. The Peltier plate removes moisture from the gas stream and condenses large hydrocarbon molecules. The ion drift tube is a ceramic tube whose external surface is coated by a layer of conductive composites to maintain a uniform DC field. An IMS Faraday plate output current and a spark discharge current can be used to quantify the NOx concentration.

BRIEF DESCRIPTION OF THE DRAWINGS

The present invention together with the above and other objects and advantages may best be understood from the following detailed description of the preferred embodiments of the invention illustrated in the drawings, wherein.

DETAILED DESCRIPTION OF THE PREFERRED EMBODIMENTS

Figure 1:
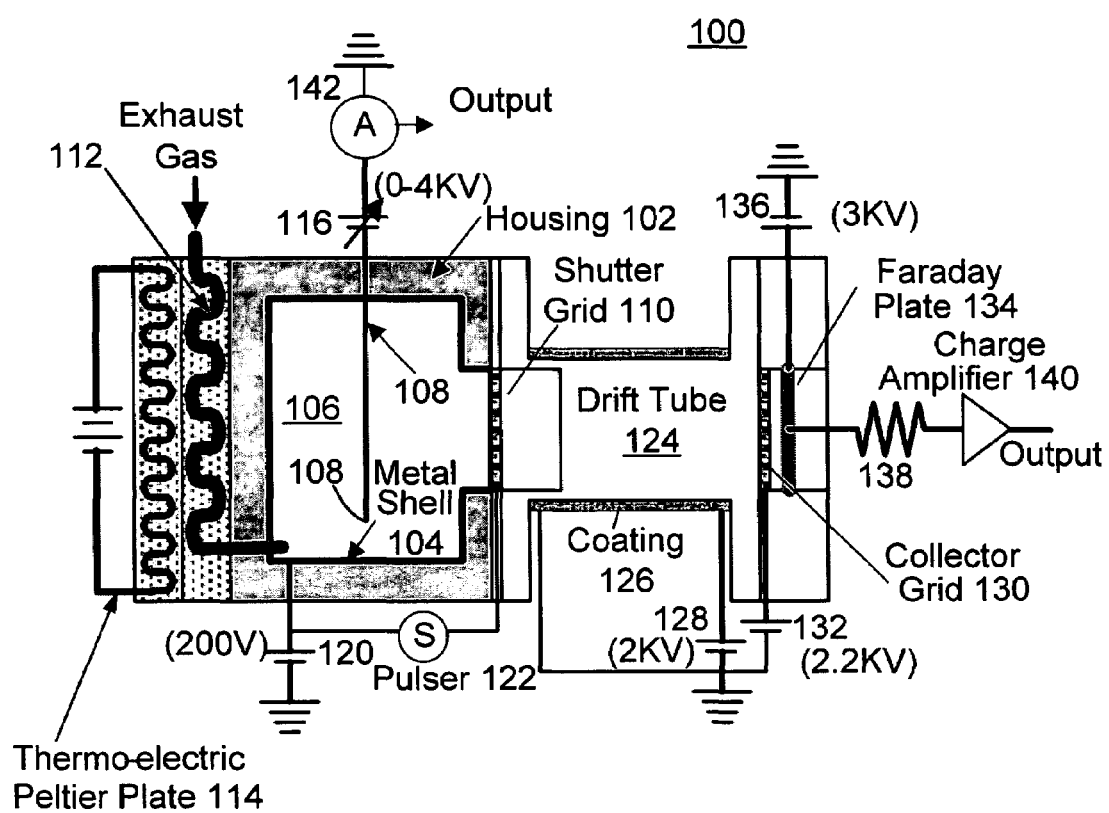
FIG. 1 is a schematic and block diagram illustrating an exemplary ion mobility spectrometry (IMS) sensor for detecting nitric oxides (NOx) in accordance with the present invention.

Having reference now to the drawings, in FIG. 1 there is shown an exemplary ion mobility spectrometry (IMS) sensor for detecting nitric oxides (NOx) in accordance with the present invention generally designated by reference character 100.

In accordance with features of the invention, IMS sensor 100 is small-sized, low-cost, robust, and reliable. IMS sensor 100 can be operated in both positive and negative modes. The negative mode of operation measures $NO_2$ in the gas stream and the positive mode of operation provides a measure of NO concentration. Control electronics provide the mode switching capability so that the total NOx concentration can be determined, where the total NOx concentration includes the negative $NO_2$ ions and positive NO ions. IMS sensor 100 can function in a harsh environment and provide a fast response.

IMS sensor 100 includes a housing 102 containing or substantially surrounding an electrically conductive cylinder or metallic shell 104 defining an ionization chamber 106. The housing 102 preferably is formed of a ceramic material, or of a ceramic and Teflon material. The ionization chamber 106 includes a spark electrode 108, such as a needle type electrode 108, the metallic shell 104, and a shutter grid 110.

IMS sensor 100 includes an exhaust gas inlet path 112 positioned proximate a thermoelectric Peltier plate generally designated by reference character 114. The thermoelectric Peltier plate 114 is used to condition the exhaust gas. The Peltier plate 114 removes moisture from the gas stream and condenses large hydrocarbon molecules.

IMS sensor 100 includes a variable voltage source 116 connected to needle electrode 108 that is used to establish a continuous spark discharge between a tip 118 of the needle electrode 108 and the metallic shell 104. A voltage source 120, such as a 200 Volt voltage source, is coupled to the metallic shell 104 and to the shutter grid 110. Also a pulser 122 is coupled to the shutter grid 110.

During operation, a continuous spark discharge is established between the tip 118 of the needle electrode 108 and the metallic shell 104. The negative $NO_2$ ions produced in the discharge region are kept inside the ionization chamber 106 by biasing the metallic shell 104 and the shutter grid 110 at a negative voltage. The positive pulse is applied to the shutter grid 110 to cause the shutter open for negative $NO_2$ ions to exit into an ion drift tube 124. The pulse frequency of the pulser 122 is selected so that equilibrium between ion production and extraction is established.

To detect positive NO ions, a positive mode of operation is used. In the positive mode of operation, opposite polarity voltages are applied as compared to the negative mode of operation. The positive NO ions produced in the discharge region are kept inside the ionization chamber 106 by biasing the metallic shell 104 and the shutter grid 110 at a positive voltage. The negative pulse is applied to the shutter grid 110 to cause the shutter open for positive NO ions to exit into an ion drift tube 124.

In accordance with features of the invention, the drift tube 124 is a ceramic tube whose external surface is coated by a layer 126 of conductive composites or resistive material to maintain a substantially uniform DC field. A voltage supply 128, such as a 2 KV voltage supply, is coupled to the layer 126 carried by the drift tube 124.

IMS sensor 100 includes a collection grid 130 connected to a voltage supply 132, such as a 2.2 KV voltage supply. A Faraday plate 134 connected to a voltage supply 136, such as a 3 KV voltage supply, is coupled via a resistor 138 to a charge amplifier 140. An output of the charge amplifier 140 corresponds to an IMS Faraday plate output current can be used to quantify the NOx concentration. Also a spark discharge current detected by a second detector 142 coupled between the voltage supply 116 and ground, can be used to quantify the NOx concentration.

Figure 2:
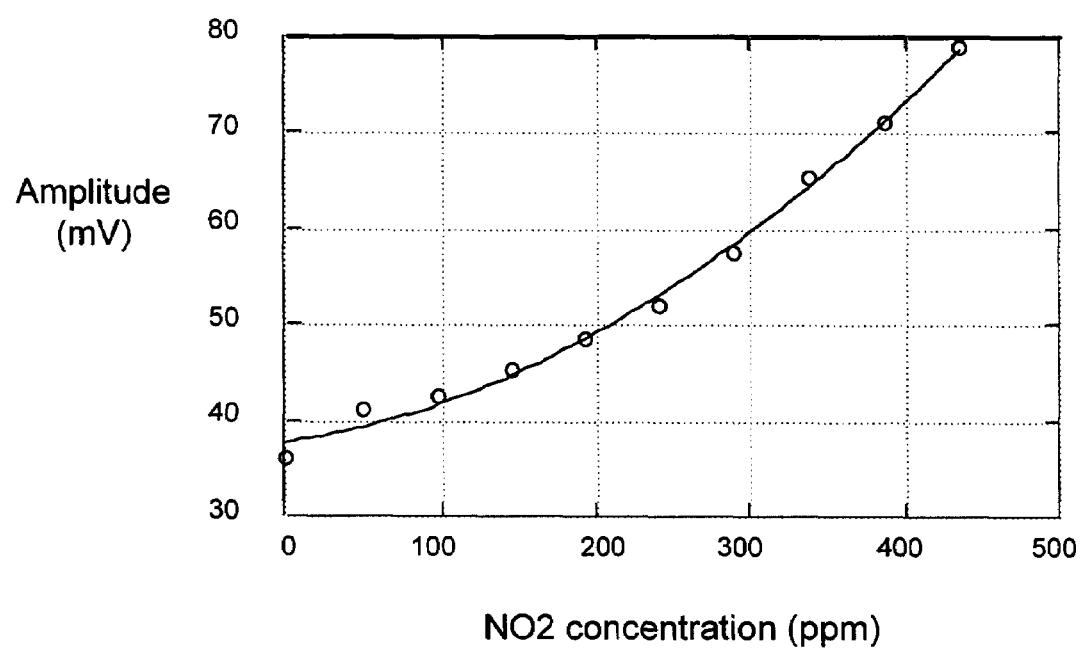
FIG. 2 is a diagram illustrating an exemplary IMS Faraday plate output current of the ion mobility spectrometry (IMS) sensor of FIG. 1 relative to $NO_2$ concentration, measured in presence of simulated exhaust gas and at 5 nA/V sensitivity, in accordance with the present invention.
Figure 3:
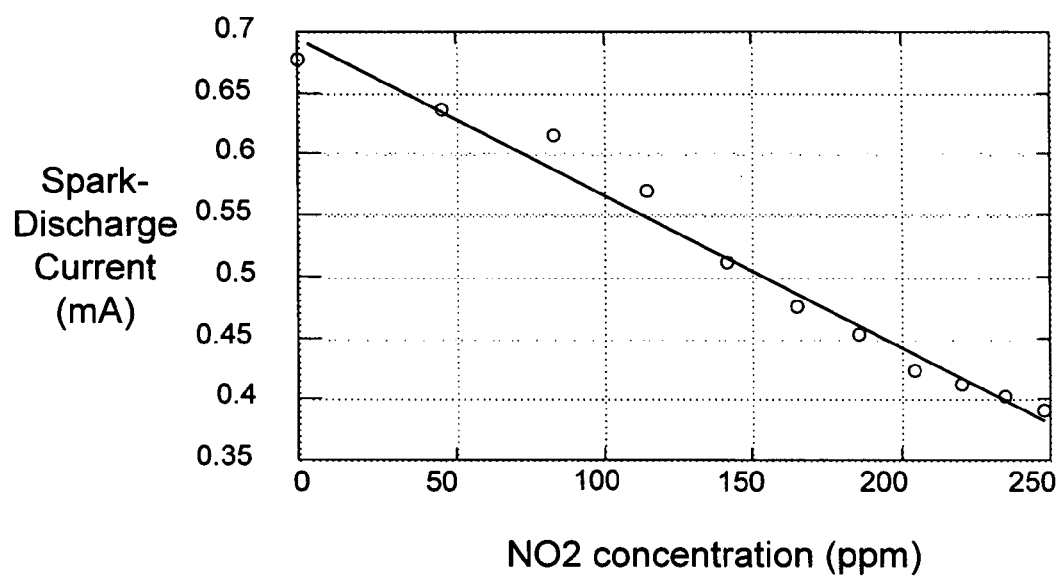
FIG. 3 is a diagram illustrating an exemplary spark discharge current of the ion mobility spectrometry (IMS) sensor of FIG. 1 relative to $NO_2$ concentration in accordance with the present invention.

FIGS. 2 and 3 respectively illustrate IMS Faraday plate output current and a spark discharge current of the IMS sensor 100. FIG. 2 illustrates a peak amplitude output vs. $NO_2$ concentration, measured in presence of simulated exhaust gas and at 5 nA/V sensitivity. FIG. 2 illustrates the spark-discharge current output vs. $NO_2$ concentration.

While the present invention has been described with reference to the details of the embodiments of the invention shown in the drawing, these details are not intended to limit the scope of the invention as claimed in the appended claims.

What is claimed is:

1. An ion mobility spectrometry (IMS) sensor for detecting nitric oxides (NOx) in an exhaust gas comprising:
   an ionization chamber for receiving the exhaust gas; said ionization chamber includes an interior electrically conductive shell;
   a spark electrode having a needle tip extending into said ionization chamber;
   a shutter grid coupled between said ionization chamber and an ion drift tube;
   means for establishing a substantially continuous spark discharge between said electrically conductive shell of the ionization chamber and said needle tip of the spark electrode for ionization of the exhaust gas.

2. An IMS sensor as recited in claim 1 includes a voltage source coupled to said electrically conductive shell of said ionization chamber and said shutter grid for biasing said electrically conductive shell and said shutter grid at a negative voltage.

3. An IMS sensor as recited in claim 1 includes a pulse generator for applying a positive pulse to said shutter grid to open said shutter grid for negative $NO_2$ ions to exit from said ionization chamber into said ion drift tube.

4. An IMS sensor as recited in claim 1 includes a collection grid and a Faraday plate coupled to said ion drift tube for detecting negative NOx ions and positive NO ions.

5. An IMS sensor as recited in claim 4 includes an output current of said Faraday plate used to quantify a NOx concentration.

6. An IMS sensor as recited in claim 1 includes a voltage source coupled to said electrically conductive shell of said ionization chamber and said shutter grid for biasing said electrically conductive shell and said shutter grid at a positive voltage.

7. An IMS sensor as recited in claim 1 includes a pulse generator for applying a negative pulse to said shutter grid to open said shutter grid for positive NO ions to exit from said ionization chamber into said ion drift tube.

8. An IMS sensor as recited in claim 1 wherein said ion drift tube is a ceramic tube having external surface coated by a layer of conductive material.

9. An IMS sensor as recited in claim 8 wherein a voltage source is coupled to said layer of conductive material to maintain a uniform DC field.

10. An IMS sensor as recited in claim 8 wherein said thermoelectric Peltier plate removes moisture from the gas stream and condenses large hydrocarbon molecules.

11. An IMS sensor as recited in claim 1 includes a thermoelectric Peltier plate for conditioning the exhaust gas received into said ionization chamber.

12. An IMS sensor as recited in claim 1 includes a spark discharge current used to quantify a NOx concentration.

13. An IMS sensor as recited in claim 1 includes a housing containing said ionization chamber and said interior electrically conductive shell.

14. An IMS sensor as recited in claim 1 wherein said housing is formed of a ceramic material.

15. A method for detecting nitric oxides (NOx) in an exhaust gas comprising the steps of:
   providing an ion mobility spectrometry (IMS) sensor having an ionization chamber for receiving the exhaust gas; said ionization chamber includes an interior electrically conductive shell; a spark electrode having a needle tip extending into said ionization chamber; a shutter grid coupled between said ionization chamber and an ion drift tube;
   establishing a substantially continuous spark discharge between said electrically conductive shell of the ionization chamber and said needle tip of the spark electrode for ionization of the exhaust gas;
   biasing said electrically conductive shell and said shutter grid at a negative voltage; and
   applying a positive pulse to said shutter grid to open said shutter grid for negative NOx ions to exit from said ionization chamber into said ion drift tube.

16. A method for detecting nitric oxides (NOx) in an exhaust gas as recited in claim 15 further includes biasing said electrically conductive shell and said shutter grid at a positive voltage; and
   applying a negative pulse to said shutter grid to open said shutter grid for positive NO ions to exit from said ionization chamber into said ion drift tube.

17. A method for detecting nitric oxides (NOx) in an exhaust gas as recited in claim 15 wherein said biasing step includes providing a voltage source coupled to said electrically conductive shell of said ionization chamber and said shutter grid.

18. A method for detecting nitric oxides (NOx) in an exhaust gas as recited in claim 15 wherein said applying step includes providing a pulse generator coupled to said shutter grid for applying said positive pulse to said shutter grid.

19. A method for detecting nitric oxides (NOx) in an exhaust gas as recited in claim 15 includes providing a Faraday plate coupled to said ion drift tube and detecting an output current of said Faraday plate to quantify a NOx concentration of the exhaust gas.

20. A method for detecting nitric oxides (NOx) in an exhaust gas as recited in claim 15 includes detecting a spark discharge current to quantify a NOx concentration of the exhaust gas.

* * * * *